US00PP37525P2

(12) United States Plant Patent
Hansen

(10) Patent No.: US PP37,525 P2
(45) Date of Patent: Jul. 21, 2026

(54) ***PENSTEMON* PLANT NAMED 'Lavender Sapphires'**

(50) Latin Name: ***Penstemon* hybrid**
Varietal Denomination: Lavender Sapphires

(71) Applicant: Hans A. Hansen, Zeeland, MI (US)

(72) Inventor: Hans A. Hansen, Zeeland, MI (US)

( * ) Notice: Subject to any disclaimer, the term of this patent is extended or adjusted under 35 U.S.C. 154(b) by 0 days.

(21) Appl. No.: 18/831,919

(22) Filed: Nov. 13, 2025

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
CPC ..... A01H 5/02
See application file for complete search history.

*Primary Examiner* — Kent L Bell

(57) ABSTRACT

The new and distinct cultivar of *Penstemon* plant named 'Lavender Sapphires' with strictly upright, tightly compact strong stems in a rounded mound, and numerous flowers with a purplish-lavender color with bluish tips flowering for about four weeks beginning in early summer and repeating in autumn if deadheaded. The lanceolate foliage is bluish-green, and the plant is winter hardy to at least USDA zones 6-8. The new plant is useful in the landscape as a specimen plant, en masse or container plant, and attractive to hummingbirds.

2 Drawing Sheets

Botanical classification: *Penstemon* hybrid.
Variety denomination: 'Lavender Sapphires'.

STATEMENT REGARDING PRIOR DISCLOSURES UNDER 37 CFR 1.77(b)(6)

The first offer for sale of *Penstemon* 'Lavender Sapphires' was by Walters Gardens, Inc. to Overdevest Nurseries, LP on Nov. 15, 2024. Walters Gardens, Inc. obtained the new plant and all information relating thereto from the inventor. No plants of *Penstemon* 'Lavender Sapphires' have been sold anywhere in the world by any name nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct plant of Beardtongue, botanically known as *Penstemon* 'Lavender Sapphires' and will be referred to hereinafter also by its cultivar name 'Lavender Sapphires' and as the new plant. The new plant of Beardtongue is a hardy herbaceous perennial grown for landscape use.

*Penstemon* 'Lavender Sapphires' is a single seedling selection derived from a cross between the proprietary unreleased hybrid known only as 13-8-9 (not patented) as the female or seed parent and the proprietary unreleased hybrid known only as 13-7-2 (not patented) as the male parent on Jun. 8, 2016, at a wholesale perennial nursery in Zeeland, Michigan. Seed was collected in late summer of 2016. All subsequent evaluations were performed in a full-sun trial garden at the same nursery with loamy sand soil and irrigation and fertilizer as required. The individual seedling was assigned the breeder code 16-1-5 while being selected for further trials during the summer of 2017. The new plant was propagated by basal shoot cuttings at the same nursery in Zeeland, Michigan in 2018, and the original plant and the cuttings were evaluated over the next four years until final approval for introduction in the summer of 2021. The resultant asexually propagated cuttings have been stable and identical to the original plant in successive asexual propagations.

SUMMARY OF THE INVENTION

*Penstemon* 'Lavender Sapphires' differs from its parents as well as all other hardy Beardtongue known to the inventor in a combination of traits. The following characteristics in combination distinguish 'Lavender Sapphires' from all other Beardtongue plants known to the inventor:

1. Round mounded growth with tightly-compact strong upright stems;
2. Glaucous lanceolate foliage developing and maintaining a slight bluish-green coloration in high light intensity;
3. Flowers of purplish-lavender with bluish tips;
4. Flowers for four weeks beginning early summer in Michigan and repeating into autumn if deadheaded;
5. Winter hardy to at least USDA zones 6 to 8.

The nearest comparison cultivars are: 'Cha Cha Purple' (not patented), 'Sweet Grapes' U.S. Plant Pat. No. 13,549, 'Crushed Grapes' U.S. Plant Pat. No. 18,233, 'Purple Riding Hood' U.S. Plant Pat. No. 23,067, 'Balrocurp' U.S. Plant Pat. No. 35,761, and 'Quartz Amethyst' (not patented).

'Cha Cha Purple' has a taller habit, less ridged panicles, and the flowers are more reddish-purple. 'Sweet Grapes' has a less branched inflorescence with fewer flowers that are darker purple. 'Crushed Grapes' has a shorter habit and the flowers are more reddish-purple. 'Purple Riding Hood' has flowers with darker purplish-red coloration. 'Balrocurp' has a shorter habit, with fewer flowers per peduncle, and the flowers are darker bluish purple. 'Quartz Amethyst' has larger flowers that are soft lavender with purple stripes and white throats. 'Balrocurp' and 'Purple Riding Hood' were less persistent in the landscape.

The female or seed parent has a shorter more open habit and bluish-colored flowers with smaller foliage. The male or pollen parent, 13-7-2, has a taller habit with more reddish flowers.

BRIEF DESCRIPTION OF THE DRAWINGS

The drawings of the new plant demonstrate the overall appearance of the plant, including the unique traits. The colors are as accurate as reasonably possible with color reproductions. Ambient light spectrum, source, temperature, and direction may cause the appearance of minor variations in color. The plant in the drawings is of a two-year-old plant grown in full sun loamy-sand soil in trial gardens of a nursery in Zeeland, Michigan.

DETAILED BOTANICAL DESCRIPTION

Figure 1:
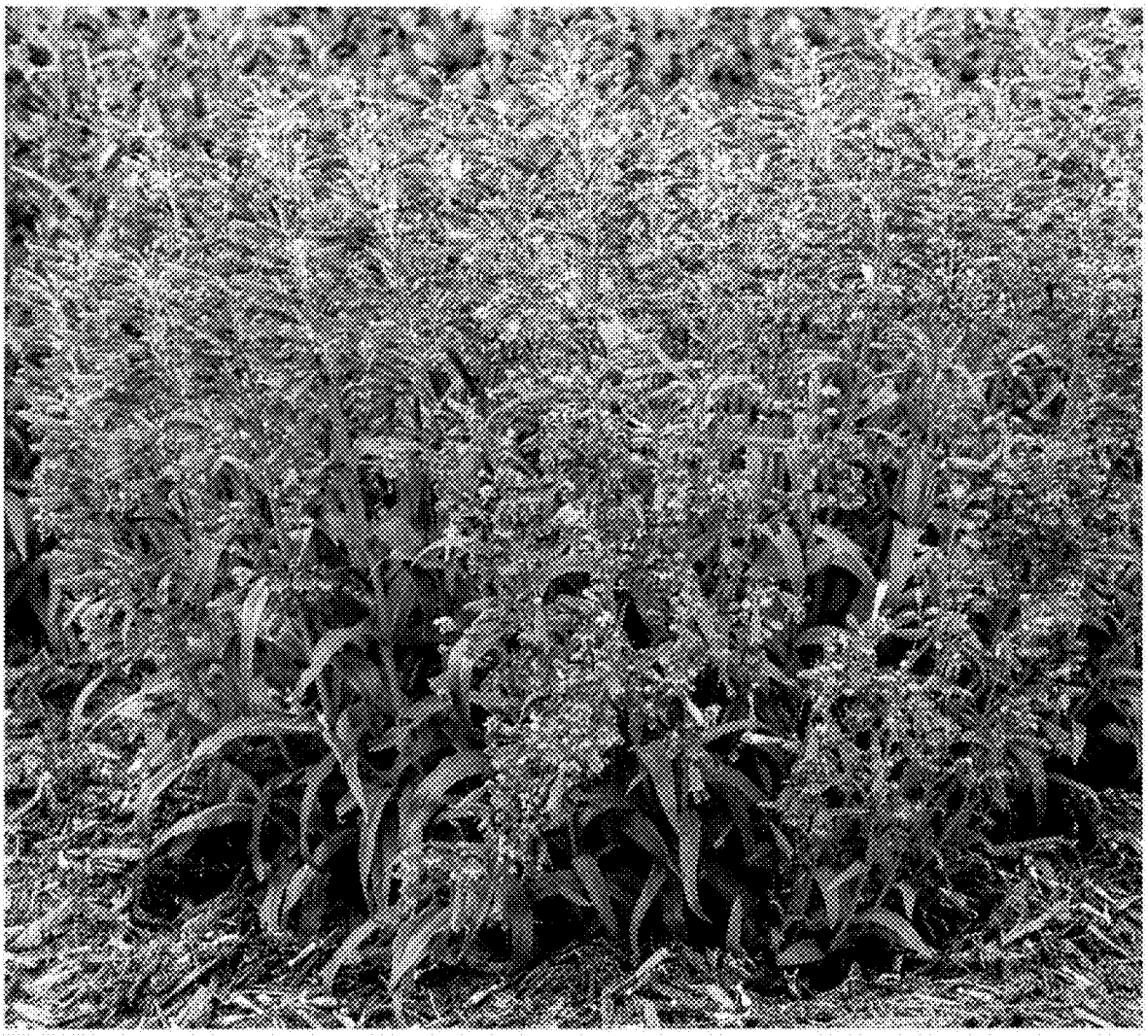
FIG. 1 shows the new plant in a trial garden landscape in early flower production.
Figure 2:
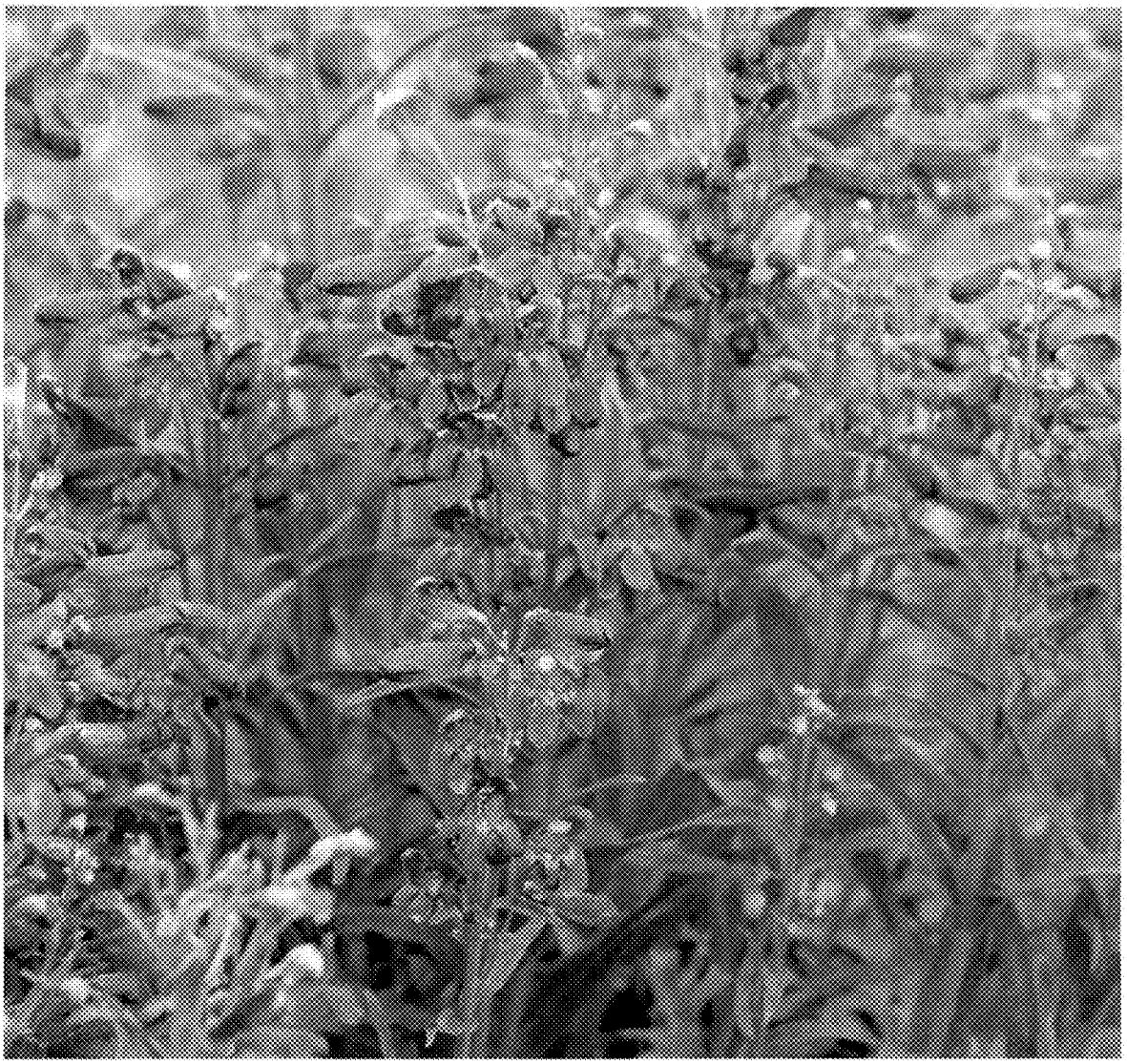
FIG. 2 shows a close-up of the flowers and buds.

The following detailed description of *Penstemon* 'Lavender Sapphires' is from two-year-old plants growing in a full-sun display garden in Zeeland, MI with limited supplemental fertilizer and irrigation as needed and without any pinching or plant growth regulators. The new plant has not been observed under all possible environments, and the phenotype may vary slightly with different environmental conditions, such as temperature, light, fertility, moisture, and maturity levels, but without any change in the genotype. The color descriptions are in accordance with the 2015 edition of The R.H.S. Colour Chart of The Royal Horticultural Society, London, England, except where common dictionary color terms are used.

Parentage: The female (seed) parent is 13-8-9 and the male (pollen) parent is 13-7-2;

Plant habit: Herbaceous winter-hardy, perennial with upright rigid stems emerging from the base in the spring; up to about 8 stems per plant; flowering in branched panicle;

Plant size: About 45 cm in height, average stem 41 cm tall, and to about 40 cm in width about 10 cm above the soil;

Root description: Fibrous, well-branched, developing to about 1 mm thick; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 3.8-liter pot from a rooted plug;

Stem description: Terete; suffruticose; highly branched distally; glabrous; glaucous; to about 6 cm long and about 4 mm diameter at base;

Stem color: Between RHS 145A and RHS 144B;

Node: About 10 per stem below peduncle branches, average internode length about 6 mm; diameter about 5 mm;

Internode color: Same as surrounding stem;

Foliage description: Opposite; simple; lanceolate; glabrous and slightly glaucous adaxial and abaxial; basal leaves with attenuate base, cauline leaves sessile and clasping; margin entire; fragrance not detected; to about 20 leaves per stem;

Leaf size: Basal leaf blades to about 13.2 cm long and about 3.2 cm wide; cauline leaves to about 12 cm long and about 1.9 cm wide;

Leaf color: Young expanding adaxial nearest RHS 144A and abaxial between RHS 144A and RHS 144B; mature adaxial between RHS N138A and RHS NN137B, abaxial nearest RHS 137B;

Leaf venation: Pinnate;

Petiole: Sessile; leaf base tapering to stem and peduncle;

Vein color: Young adaxial midrib and primary veins nearest RHS 145A, young abaxial midrib and secondary veins nearest RHS 145C; mature adaxial midrib nearest RHS 146A and secondary veins nearest RHS 137A, abaxial midrib distally between RHS 146D and RHS 145A and midrib proximally nearest RHS 145C, abaxial primary veins nearest RHS 147C;

Inflorescence: About 20 per plant; heavily-branched panicle; flowering portion to about 22 cm long and about 9.5 cm across;

Pedicel: Cylindrical; matte; glabrous; size in length between 5 and 13 mm long, and 1 mm diameter;

Pedicel color: Between RHS 144B and RHS N144D;

Peduncle: Panicle; cylindrical; glabrous; smooth; with up to twelve branches; main stems aspect vertical; to about 48 cm tall and 5 mm diameter base; flowering in upper 22 cm; about 18 branches to about 18 cm long and 1.5 mm diameter; to about 125 flowers per stem and 27 flowers per branch;

Peduncle color: Nearest RHS 146D with portions getting high sun exposure moderately blushed to solid nearest RHS 187A;

Flower buds about one day prior to opening: Clavate; rounded apex; with rounded base; about 27 mm long, about 6 mm wide distally, and 3 mm diameter near the base; basal 3 mm of corolla tube narrowed to about 3 mm diameter;

Bud color: Proximal 3 to 4 mm of corolla tube between RHS 76A and RHS 76B, and distal 3 mm between RHS N95A and RHS N95B, ventral central portion variable nearest RHS N80B and nearest RHS 94B with veins of nearest RHS N81B, dorsal central portion lighter than RHS 85D with veins nearest RHS 86D;

Flowering season: Beginning in early June to early July and flowering for about four weeks, repeating if deadheaded;

Flowers: Single; zygomorphic; perfect; complete; bilabiate with upper and lower lip gamopetalous in about the basal 23 mm; about 33 mm long and about 15 mm across and 14 mm tall at the face; lower labium face flat when first open becoming slightly reflexed, upper labium continuing straight; lasting about five to seven days; self-cleaning;

Flower attitude: Mostly outward;

Flower fragrance: None detected;

Corolla: Bilabiate; ventral petal with three lobes; dorsal petal with two lobes; glabrous abaxial; glabrous adaxial dorsal petal and fused tube portion, except pubescent on an adaxial ventral petal in the distal portion near mouth; dorsal petal lobes about 2 mm long and 2 mm across at fusion with rounded apices; two ventral lobes side lobes about 7 mm long and 4 mm wide at division just beyond midpoint between fusion and apex, center ventral lobe about 7 mm long and 4 mm across; all lobes with rounded apices and entire margins; corolla tube about 33 mm long and about 15 mm across at outside lobes, 6 mm across at fusion, 14 mm tall at the face, and 3 mm diameter at base;

Corolla color: Adaxial-dorsal and ventral labia in the proximal 2 mm of corolla tube nearest RHS 145D, the center 13 mm or dorsal labium between RHS N82D and RHS 84D, the center 13 mm of ventral labium between RHS N82D and RHS 84D with veins of between RHS 77A and RHS 83B, distal 7 mm including lobes of dorsal labium nearest RHS 95B, distal 7 mm including lobes of ventral labium nearest RHS 93B;

Abaxial: Dorsal and ventral labia in the proximal 2 mm nearest RHS 145D, center 15 mm of dorsal labium between RHS 91A and RHS 90D with veins nearest RHS N81B, center 15 mm of ventral labium between RHS 84D and RHS NN155D with veins of between RHS N81A and RHS N81B, distal 6 mm including lobes or dorsal labium nearest N95C, distal 6 mm including lobes of ventral labium nearest RHS 93B;

Gynoecium: Single; superior; persistent after corolla drops; about 24 mm long;

*Style*.—Cylindrical; glabrous; lustrous; arcuate slightly downwardly distally; about 19 mm long and about 0.5 mm diameter; color nearest RHS NN155B proximally transitioning to nearest RHS 72A in the distal half.

*Stigma*.—Semi-globose, to about 0.5 mm diameter; color nearest RHS N155C.

*Ovary*.—Oblong conical; with truncate base and acute apex; about 5 mm long and 2 mm across at base; color nearest RHS 146D.

Androecium: Four; didynamous; slightly arcuate;

*Filaments*.—Longer set about 26 mm long and adnate inner corolla in basal 11 mm, shorter set about 23 mm long adnate inner corolla in basal 2 mm, about 1 mm in diameter; color nearest RHS NN155B with the proximal 2 mm nearest RHS 145C.

*Anther*.—Elliptic; basifixed; longitudinal; bent at filament attachment; about 4 mm long and 1.5 mm across; color nearest RHS 158A with a slight blush of nearest RHS 72B.

*Staminode*.—Single; cylindrical; about 22 mm long and 0.5 mm diameter; adnate to inner corolla tube in basal 7 mm; tufted in distal 2 mm.

*Staminode color*.—Proximal 3 mm nearest RHS 145C, distally nearest RHS NN155B.

*Pollen*.—Abundant; color nearest RHS NN155B.

Calyx: Campanulate; adpressed to corolla; about 6 mm long and about 5 mm across at apex;

Sepals: Five; lanceolate; glabrous adaxial and abaxial; acute apex and fused in basal 2 mm; entire margin; to about 2 mm wide above fusion point and 6 mm long;

Sepal color: Adaxial and abaxial between RHS 137D, RHS 138A and RHS 146B with margins between RHS 145D and RHS 155C;

Fruit: Septicidal capsule; ovoid with acute apex and rounded base; to about 12 mm long and 6 mm across; color with maturity nearest RHS N199B;

Seed: Irregular; flattened, dried; about 0.7 mm across and about 0.3 mm thick; color nearest RHS 200A;

*Hardiness from at least U.S.D.A. zones* 6 *to* 8.—The new plant performs best with good drainage and is resistant to drought once established.

*Pest and disease resistance*.—Resistance beyond that typical of Beardtongue plants has not been observed. No other susceptibility or resistance to diseases or pests has been observed except that which is common to *Penstemon*.

It is claimed:

1. A new and distinct cultivar of *Penstemon* plant named 'Lavender Sapphires' as herein described and illustrated.

* * * * *